United States Patent [19]

Hashimoto

[11] 4,351,743
[45] Sep. 28, 1982

[54] DILUTE STANDARD GASES PREPARED BY UTILIZING BUFFERED SOLUTION, METHOD FOR PREPARATION THEREOF AND APPARATUS THEREFOR

[76] Inventor: Yoshikazu Hashimoto, 7-3-14, Minamiaoyama, Minato-ku, Tokyo, Japan

[21] Appl. No.: 783,458

[22] Filed: Mar. 31, 1977

[30] Foreign Application Priority Data

Apr. 7, 1976 [JP] Japan .................................. 51-38149

[51] Int. Cl.$^3$ ............................................. C09K 3/00
[52] U.S. Cl. ................................. 252/408; 23/230 R; 23/232 R
[58] Field of Search ......... 252/408; 23/230 R, 232 R, 23/230 A

[56] References Cited

U.S. PATENT DOCUMENTS

| | | | |
|---|---|---|---|
| 3,466,249 | 9/1969 | Anderson | 252/408 |
| 3,681,255 | 8/1972 | Wilfore | 252/408 |
| 3,721,253 | 3/1973 | Remke et al. | 23/230 A |
| 3,804,595 | 4/1974 | Scott | 252/408 |
| 3,859,049 | 1/1975 | Ware et al. | 252/408 |
| 4,001,142 | 1/1977 | Turner | 252/408 |
| 4,042,333 | 8/1977 | Dell et al. | 23/232 R |
| 4,126,575 | 11/1978 | Louderback | 252/408 |
| 4,163,734 | 8/1979 | Sorenson | 252/408 |
| 4,188,190 | 2/1980 | Murahi et al. | 23/232 R |

*Primary Examiner*—J. L. Barr
*Attorney, Agent, or Firm*—Wenderoth, Lind & Ponack

[57] ABSTRACT

Dilute standard gases are prepared by utilizing a buffered solution of a compound capable of generating a desired gas. The pH of the solution adjusted so as to provide a solution with a desired specific vapor pressure of said gas and said gas is absorbed by a flow of air passed through the vapor phase above the solution. An apparatus for the performance of said process is also provided.

3 Claims, 4 Drawing Figures

DILUTE STANDARD GASES PREPARED BY UTILIZING BUFFERED SOLUTION, METHOD FOR PREPARATION THEREOF AND APPARATUS THEREFOR

BACKGROUND OF THE INVENTION

This invention relates to a method of preparation of a dilute standard gas, said gas itself and an apparatus for the performance of said method.

Many difficulties have been encountered in conventional methods for preparation of a dilute standard gases used, for example, in the calibration of standards in gas microanalysis and also for the calibration of automatic, continuous gas analyzers.

Among the difficulties encountered in conventional methods there may be mentioned inevitable errors resulting from unrepresentative sampling of a given gas, unhomogeneous mixing of said gas with a diluent, loss of gas by the absorption thereof onto the surface of receiver vessel and also a change of concentration of gas due to the generation of the target (desired) gas itself or due to the instability of the gas.

Among the many methods which have been hitherto proposed to provide accurate, dilute standard gases, the permeation tube method is considered to be most superior and widely used. The permeation tube consists of a tube of a polymeric substance such as Teflon containing a liquified or a highly compressed gas to be used in the preparation of the standard gas.

Both ends of the permeation tube are sealed. Since the vapor pressure of the gaseous sample in the inside of the tube becomes high, a small amount of the gas is always purged through the wall of the tube. If the temperature of the tube is constant, the amount of purged gas per unit time becomes constant. The permeation tube is then placed in a fresh air flow of a definite flow rate at a constant temperature to provide a dilute gas of definite concentration.

The permeation tube method has advantages such as the fact that it is possible to directly generate a very small amount of gas at a constant rate and moreover it is, of course, possible to determine the absolute rate of gas generation from the permeation tube, merely by measuring the weight loss of the tube.

On the other hand, the permeation method has several disadvantages in practice, although the basic principle of the method is rather simple. The main disadvantages include the necessity to carefully regulate the temperature of the air flow since the rate of generation of gas from the tube changes drastically with a small change of the temperature, a rather long time lag to obtain a gas flow of a constant concentration after the beginning of the flow of air and the need for skill in the preparation of the permeation tube, despite the simplicity of the principle.

SUMMARY OF THE INVENTION

The primary object of the present invention is to provide a method for the preparation of a dilute standard gas free from the above disadvantages encountered in the permeation tube method.

The above objective and others are realized by the present invention as follows:

A solution of a compound which is able to generate a target gas is prepared. The pH of the solution is adjusted by a buffer e.g. solution in order to obtain the target gas at a constant vapor pressure from the solution.

Simultaneously, an air flow is passed through the vapor from the liquid phase of the solution at a constant rate. It is not necessary that an air flow must be passed at "a constant rate" in order to take up the target gas in a desired amount. Thus, various kinds of dilute standard gases can be prepared.

The advantageous features of this method are as follows:

(1) It is possible to generate a dilute standard gas to any desired concentration.

(2) It is possible to continuously produce a standard gas of a desired definite concentration over a long period.

(3) As in the permeation tube method, it is possible to determine the absolute rate of gas generation by measurement of change of the concentration of the gas generation solution.

(4) The reproducibility of a dilute standard gas having a desired concentration is very superior.

(5) The time lag to obtain a standard gas having a desired definite concentration, after the beginning of the flow of gas, is rather short.

(6) The regulation of temperature is not very critical.

(7) No special apparatus is required.

(8) The operation is simple and does not demand skilled operators for its performance.

(9) The present invention can be applied to the preparation of dilute standard gases such as nitrogen oxides, sulfur oxides, hydrogen sulfide, hydrogen cyanide and other inorganic gases as well as formaldehyde and other organic gases.

DETAILED DESCRIPTION OF THE INVENTION

The method of preparation of dilute standard gas of the present invention will be further explained with reference to the preparation of a dilute standard of gaseous hydrogen cyanide. It is generally considered that, even though it is a standard gas of high concentration, the preparation of hydrogen cyanide gas of a definite concentration is not a simple matter.

EXAMPLE

Apparatus and Reagents

Hydrogen cyanide gas analyzer: a digital pH meter (Type HM-20B manufactured by the Toa Electrotech. Corp.), a selective electrode for cyanide use (Type CN-125 manufactured by the Toa Electrotech. Corp.) and a reference electrode (Type HC-305D manufactured by the Toa Electrotech. Corp.).

Thermostat of aqueous medium type: capable of regulating the temperature between about +5 and 80° C. within an accuracy of ±0.08° C.~±0.12° C. (Type Thermomeit TH-11 manufactured by the Yamato Scientific Corp.).

Flow meter: a flow meter (100~1400 ml/min) (Type FT-1/8-4-150 manufactured by the Kusano Scientific Corp.) and an orifice flow meter of the mercury type.

Reagents: potassium cyanide and sodium hydroxide (both reagents used in the following experiments were of a special reagent grade produced by the Kokusan Chem. Corp.).

Buffer solutions:
a solution of pH=7.0
  ... this solution is prepared by dissolving 6.80 g of potassium dihydrogenphosphate and 1.19 g of sodium hydroxide into water to obtain 1 l of solution.
a solution of pH=8.9
  ... this solution is prepared by dissolving 3.1 g of boric acid, 3.73 g of potassium chloride and 0.85 g of sodium hydroxide into water to obtain 1 l of solution.
a solution of pH=11.0
  ... this solution is prepared by dissolving 17.5 g of disodium hydrogen phosphate ($Na_2HPO_4 \cdot 12H_2O$) and 0.33 g of sodium hydroxide into water to obtain 1 l of solution.
a solution of pH=11.9
  ... this solution is prepared by dissolving 17.9 g of disodium hydrogenphosphate ($Na_2HPO_4 \cdot 12H_2O$) and 1.728 g of sodium hydroxide into a water to obtain 1 l of solution.

A ribbon heater or the like is desirably provided.

Experimental Apparatus and Operation

Figure 1:
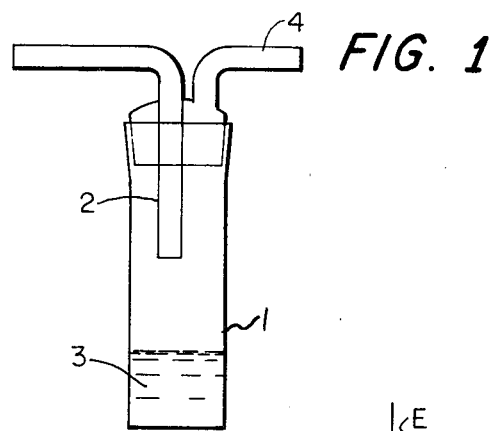
FIG. 1 depicts a schematic side elevational view of a gas generating bottle used in the method.
Figure 2:
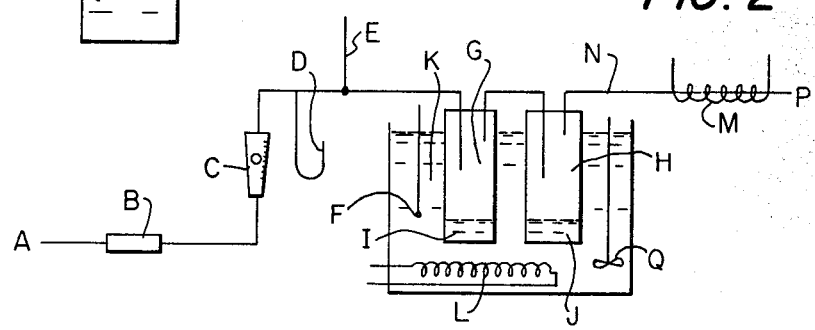
FIG. 2 is a diagrammatic depiction of the gas generating apparatus.

The main numerals and letters employed in FIGS. 1 and 2 are summarized here for convenience.

(1) gas absorbing bottle of 30 ml capacity, (2) gas inlet tube, (3) gas generating liquid, (A) air inlet, (B) layers of air purifying agent, (C) flow meter, (D) manometer, (E) thermometer, (F) thermometer, (G) preheating chamber, (H) gas generating chamber, (I) distilled water for humidity control, (J) gas generating liquid, (K) thermostatically controlled water bath, (L) heater, (M) ribbon heater, (N) gas exit tube, (P) gas collecting means and (Q) agitator.

With reference to FIG. 1, a commercially available gas absorbing bottle (1) of 30 ml capacity of a bottle of the Greenburg Smith type is employed as the gas generating chamber. The surface of gas generating liquid (3) is adjusted so as not to contact the center of the gas introduction tube (2) when the liquid is charged in the bottle. Gas is removed via exit tube (4).

The arrangement of a standard gas generating apparatus is depicted in FIG. 2, wherein a gas generating chamber (H) containing a gas generating liquid (J) consisting of a mixture of a pH buffer solution and a potassium cyanide solution is partially immersed in a water bath (K) which is thermostatically maintained at 40° C. A purified air flow supplied from an inlet (A) and passed through gas purifying layers (B) and is introduced into the gas generating chamber (H) through a preheater chamber (G) and it passes through at a constant rate (in this example, it was 300 ml/min) over the surface of the gas generating solution (J). A gas exit tube (N) which permits removal of the air flow from the gas generating chamber (H) is heated by a ribbon heater (M). Thus, the air flow removed from the gas exit tube (N) by gas collecting means (P) contains the target or object gas in a desired amount and is suitable for use as a dilute standard gas.

The flow rate of the air flow is measured by a flow meter (C) and the observed value is corrected to the standard state using the observed temperature and pressure indicated by a thermometer (E) and a manometer (D), respectively.

The concentration of hydrogen cyanide contained in the obtained standard gas can be determined analytically using a cyanide ion selective electrode after dissolving the cyanide gas contained in the standard gas into an aqueous solution of sodium hydroxide.

In FIG. 2, (I) is distilled water provided in a preheater (G), to be used for humidity control, (L) is a heater, (Q) is an agitator.

Results and Interpretation Thereof

A series of experiments were carried out using aqueous solutions of potassium cyanide whose concentrations were 60, 30, 10 and 5 $\mu g/ml$ and adjusting the pH of each solution to 7.0, 8.9, 11.0 and 11.9. From those experiments, it was found that the amount of hydrogen cyanide generated from a solution of any concentration of potassium cyanide rapidly decreases when the pH of the solution exceeds 11.0.

The concentration of potassium cyanide in the gas generating solution, $C_{sol}(\mu g/ml)$ and the concentration of the target gas in the air flow, $C_{air}(ppm)$, exhibit a linear relation if plotted on a log-log paper, that is, the relation can be expressed by the following equation (1), $$C_{air} = k \cdot C_{sol}^n \qquad (1)$$

wherein, n is the inclination of the said straight line and k is the value of $C_{air}$ when $C_{sol}=1$. Moreover, such relation between n and k as depicted in Table 1 was found at various pH values when the concentration of potassium cyanide in a gas generating solution was 350 $\mu g/ml$ and the flow rate of the air flow was 300 ml/min.

TABLE 1

| Examples of n and k in Eq. (1) (HCN) | | |
| --- | --- | --- |
| pH | n | k |
| 7.0 | 0.98 | 0.48 |
| 8.9 | 0.98 | 0.44 |
| 11.0 | 0.96 | 0.058 |
| 11.9 | 0.90 | 0.014 |

Figure 3:
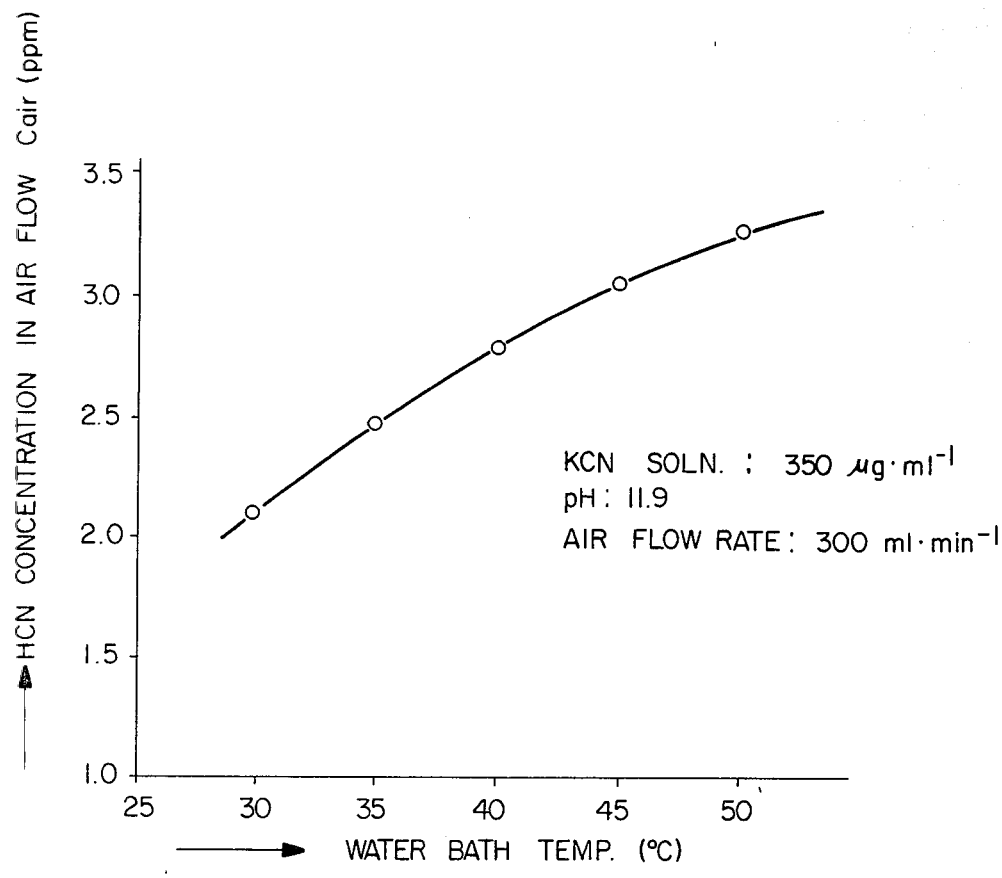
FIG. 3 is a graph depicting the relationship between the concentration of hydrogen cyanide gas in the air flow and the temperature of a water bath controlled by a thermostat provided in the gas generating apparatus to control the temperature of gas generation and FIG. 4 depicts the change of concentration in air ($C_{air}$) of hydrogen cyanide gas in an air flow (passing through the vapor phase of the gas generating solution) against time.

The relation between the temperature of gas generating liquid and $C_{air}$ is depicted in FIG. 3, wherein the concentration of potassium cyanide was 350 $\mu g/ml$, the pH value was 11.9 and the flow rate of air was 300 ml/min. The relationship depicted in FIG. 3 is nothing but a type of vapor pressure curve from this figure, it can be understood that the increase of $C_{air}$ with the increase of the temperature is rather gradual, if compared with such relation in the permeation tube method.

Figure 4:
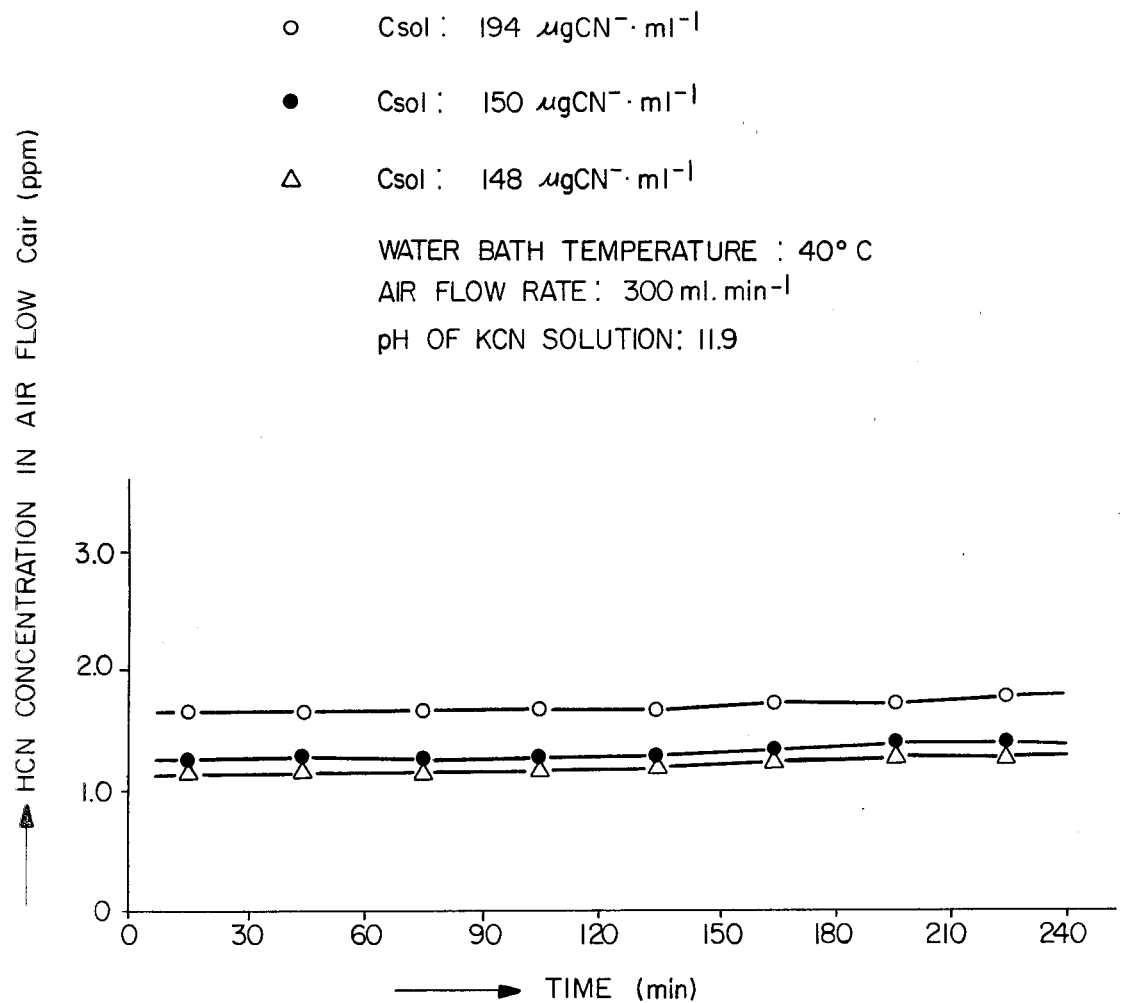

The change of $C_{air}$ value with respect to time is shown in FIG. 4, wherein three different concentrations of $C_{sol}$ were employed, i.e. 148, 150 and 194 $\mu g/ml$. The temperature, flow rate of air and pH were at constant values, e.g. 40° C., 300 ml/min and 11.9, respectively.

In the figure, it can be seen that, in the initial stage of about 100 minutes, the change of the concentration $C_{air}$ was within the range of experimental error for the measurement of cyanide ion concentration, using the ion selective electrode and after 100 minutes, a small increase of the temperature was confirmed.

The fact that the concentration $C_{air}$ slightly increases with respect to time may be due to a natural increase in the concentration $C_{sol}$.

From these observations, the following can be presumed.

(1) There is hardly any decrease of the concentration of potassium cyanide in the gas generating liquid during the use of said liquid.

(2) The agitation of the gas generating liquid due to convection occurs.

(3) Under the experimental conditions, the concentration of the gas generating liquid due to the evaporation of water therefrom occurs more rapidly than the dilution of the liquid due to the escape of hydrogen cyanide therefrom.

Furthermore, methods for the production of standard gases other than hydrogen cyanide were successfully carried out. In this regard, the results of two experiments to produce dilute standard gases, nitrogen oxide (NOx) and sulfur dioxide (SO₂), which gases are very detrimental to environmental quality, are shown in Table 2.

TABLE 2

| Data for Generation of $NO_x$ and $SO_2$ | | | | | | |
|---|---|---|---|---|---|---|
| Type of gas generated | Gas generating Compound | Rate of Air Flow ml/min | Temperature °C. | pH | n | k |
| Nox | NaNO₂ | 910 | 25.0 | 5.0 | 0.73 | 0.015 |
| SO₂ | NaHSO₃ | 300 | 25.0 | 4.3 | — | — |

I claim:

1. A method for generating a dilute standard gas selected from the group consisting of nitrogen oxides, sulfur oxides, hydrogen sulfide, hydrogen cyanide and formaldehyde at a substantially constant rate which comprises:
   (a) preparing a solution containing a compound capable of generating said gas;
   (b) adjusting the pH of said solution with a buffer, in a gas generating chamber having gas introduction and exit tubes disposed above said solution, to generate gas into the vapor phase above said solution;
   (c) passing a flow of air into said gas generating chamber through said gas introduction tube and removing dilute standard gas through said exit tube,
   said gas generating chamber being maintained at a substantially constant temperature throughout said gas generation, whereby said gas is generated at a substantially constant rate and is taken up by said flow of air at a substantially constant rate.

2. A method according to claim 1 wherein said gas generating compound is potassium cyanide, sodium nitrate or potassium bisulfite.

3. A method according to claim 2 wherein said gas is hydrogen cyanide and said buffer comprises sodium hydroxide in combination with one of potassium dihydrogenphosphate potassium chloride or disodium hydrogen phosphate and said gas generating compound is potassium cyanide.

* * * * *